United States Patent
Newsome, Jr. et al.

(10) Patent No.: US 11,607,372 B2
(45) Date of Patent: Mar. 21, 2023

(54) DEPILATORY WAX ADDITIVE AND PROCESS

(71) Applicant: Mermaid Brand Holdings, LLC, Leander, TX (US)

(72) Inventors: Norman D. Newsome, Jr., Leander, TX (US); Kristen D. Newsome, Leander, TX (US)

(*) Notice: Subject to any disclaimer, the term of this patent is extended or adjusted under 35 U.S.C. 154(b) by 177 days.

(21) Appl. No.: 17/220,602

(22) Filed: Apr. 1, 2021

(65) Prior Publication Data

US 2022/0040049 A1 Feb. 10, 2022

Related U.S. Application Data

(60) Provisional application No. 63/062,119, filed on Aug. 6, 2020.

(51) Int. Cl.
| | | |
|---|---|---|
| *A61Q 9/04* | (2006.01) | |
| *A61K 8/02* | (2006.01) | |
| *A61K 8/31* | (2006.01) | |
| *A61K 8/92* | (2006.01) | |
| *A61K 8/81* | (2006.01) | |
| *A61K 8/26* | (2006.01) | |
| *A61Q 19/00* | (2006.01) | |

(52) U.S. Cl.
CPC .............. *A61K 8/0204* (2013.01); *A61K 8/26* (2013.01); *A61K 8/31* (2013.01); *A61K 8/8135* (2013.01); *A61K 8/92* (2013.01); *A61Q 9/04* (2013.01); *A61Q 19/00* (2013.01); *A61K 2800/28* (2013.01); *A61K 2800/75* (2013.01); *A61K 2800/805* (2013.01); *A61K 2800/882* (2013.01)

(58) Field of Classification Search
None
See application file for complete search history.

(56) References Cited

U.S. PATENT DOCUMENTS

| 9,801,810 | B1* | 10/2017 | Dugalic | A61Q 9/04 |
| 2007/0248563 | A1 | 10/2007 | Iovanni et al. | |
| 2008/0118457 | A1* | 5/2008 | Acher | A61K 8/922 |
| | | | | 424/73 |
| 2012/0138078 | A1 | 6/2012 | Ricard | |
| 2015/0125403 | A1 | 5/2015 | Joerger et al. | |
| 2018/0028419 | A1* | 2/2018 | Saaid | A61K 8/92 |

FOREIGN PATENT DOCUMENTS

CA 2567117 C 12/2005

OTHER PUBLICATIONS

"Glitter Wax Creations" available as of Mar. 31, 2021 at: https://www.glitterwaxcreations.com/; 1 pg.
Nicole, Heather; "Live Love Beauty" available as of Feb. 4, 2021 at: https://www.livelovebeauty.com/; pp. 1-7.

* cited by examiner

*Primary Examiner* — Brian Gulledge
(74) *Attorney, Agent, or Firm* — Bracewell LLP; Brian H. Tompkins

(57) ABSTRACT

A depilatory wax additive and process. The depilatory wax additive may modify a depilatory hard wax composition to include visual, olfactory, or skin treatment components. A depilatory wax additive may include molded hard wax component and glitter, a color modifier, a scent modifier, or a skin treatment. A preexisting hard wax composition of solid particles may be heated to a liquid. The depilatory wax additive may be added to the liquefied preexisting hard wax composition, mixed, and heated to disperse the glitter, a color modifier, a scent modifier, or a skin treatment in the wax mixture.

8 Claims, 3 Drawing Sheets

DEPILATORY WAX ADDITIVE AND PROCESS

CROSS-REFERENCE TO RELATED APPLICATIONS

This application claims priority from U.S. Provisional Application No. 63/062,119 filed Aug. 6, 2020, and titled "DEPILATORY WAX ADDITIVE AND PROCESS." For purposes of United States patent practice, this application incorporates the contents of the Provisional Application by reference in its entirety.

BACKGROUND

Field of the Disclosure

The present disclosure generally relates to depilatory waxes. More specifically, embodiments of the disclosure relate to additives and process for visual, olfactory, and skin treatment enhancement of depilatory waxes.

Description of the Related Art

Depilatory waxes are applied to the skin to remove hair. After application to the skin, some waxes (referred to as "soft waxes") remain relatively soft at room temperature and are removed via a muslin strip. Other waxes (referred to as "hard waxes) harden at room temperature and are removed without the use of a muslin strip.

SUMMARY

As used herein, the term "hard wax" refers to a depilatory wax that is a solid at room temperature but liquefies after heating. Hard waxes may have unappealing visual and olfactory characteristics. Users of such waxes and customers of waxing salons may desire a hard wax with more appealing visual or olfactory characteristics, especially during application of the wax during hair removal. Hard waxes may also irritate the skin and leave inflammation, itchiness, or other discomfort in the area of hair removal.

Embodiments of the disclosure generally relate to depilatory wax additive and process for modifying a hard wax to include various visual, olfactory, or skin treatment characteristics.

Advantageously, the depilatory wax additive and process reduces the time and difficulty of preparing and using a hard wax composition with appealing visual or olfactory characteristics or with a skin treatment. For example, the depilatory wax additive and process eliminates the underuse or overuse of visual, olfactory, or skin treatment components and reduces or eliminates waste during the addition to a hard wax composition and during application of the hard wax composition to skin for hair removal. Additionally, the depilatory wax additive provides a concentrated amount of the visual, olfactory, or skin treatment components and enables easier mixing with a preexisting hard wax composition. Further, embodiments of the disclosure eliminates the need for a user to buy multiple hard wax formulations that contain one or more of the desired combinations. The use of a depilatory wax additives with one or more of the desired components may reduce costs and storage requirements for wax supplies, as well as reducing the time required to mix and apply the wax. For example, preexisting hard wax may be purchased in bulk (e.g., in the form of pellets, beads, or other solid particles) to reduce cost, and various embodiments of the depilatory wax additive may be used to modify the preexisting hard wax as desired.

The depilatory wax additive may be used by a user to modify or add various components to a preexisting hard wax composition. For example, a typical user of depilatory waxes may obtain a preexisting hard wax composition in the form of pellets, beads, or other solid particles that does not lend itself to additives. The depilatory wax additive may be used to modify or add visual, olfactory, or skin treatment components to the preexisting hard wax composition, enabling a user to use any preexisting (i.e., "off-the-shelf") hard wax composition and add any visual, olfactory, or skin treatment components that they desire.

Advantageously, embodiments of the depilatory wax additive that include glitter provide for a relatively uniform dispersal of glitter in a wax mixture as compared to the addition of loose glitter to a liquefied wax. The uniform dispersal enables the glitter to remain suspended and relatively uniform in a liquefied wax as the wax is applied to the skin for hair removal. Moreover, other components, such as a color component, a scented component, or a skin treatment, may be uniformly dispersed in the liquefied wax as compared to the addition of these individual components alone to a liquified hard wax.

In one embodiment, a method for using a depilatory wax composition is provided. The method includes obtaining a depilatory wax additive, the depilatory wax additive having a molded hard wax composition and glitter, and obtaining a depilatory wax composition having solid particles. The method further includes heating the depilatory wax composition to form a liquefied wax composition and mixing the depilatory wax additive with the liquefied wax composition to form a wax mixture. Finally, the method includes heating the wax mixture until the depilatory wax additive liquefies, such that the glitter is dispersed in the wax mixture to form a liquefied wax mixture having the glitter.

In some embodiments, the method includes applying the liquefied wax mixture to skin for hair removal. In some embodiments, the method includes removing the liquefied wax mixture from the skin to remove hair from the skin. In some embodiments, the depilatory wax additive has a hard wax to glitter volumetric ratio of 3:1 to 5:1. In some embodiments, the weight ratio of the depilatory wax additive to the depilatory wax composition is 1:80 to 1:160.

In another embodiment, a depilatory wax additive is provided that includes a molded hard wax composition and glitter. In some embodiments, the depilatory wax additive has a hard wax to glitter volumetric ratio of 3:1 to 5:1. In some embodiments, the molded hard wax composition includes polycyclopentadiene, microcrystalline wax, an ethylene-vinyl acetate (VA) copolymer, paraffin, and calcium aluminum borosilicate.

In another embodiment, a method for using a depilatory wax composition is provided. The method includes obtaining a depilatory wax additive, the depilatory wax additive having a molded hard wax composition and a color component, and obtaining a depilatory wax composition having solid particles. The method further includes heating the depilatory wax composition to form a liquefied wax composition and mixing the depilatory wax additive with the liquefied wax composition to form a wax mixture. Finally, the method includes heating the wax mixture until the depilatory wax additive liquefies, such that the color component is dispersed in the wax mixture to form a liquefied wax mixture having the color component.

In some embodiments, the method includes applying the liquefied wax mixture to skin for hair removal. In some embodiments, the method includes removing the liquefied wax mixture from the skin to remove hair from the skin. In some embodiments, the weight ratio of the depilatory wax additive to the depilatory wax composition is 1:80 to 1:160.

In another embodiment, a depilatory wax additive is provided that includes a molded hard wax composition and a color component. In some embodiments, the molded hard wax composition includes polycyclopentadiene, microcrystalline wax, an ethylene-vinyl acetate (VA) copolymer, paraffin, and calcium aluminum borosilicate.

In another embodiment, a method for using a depilatory wax composition is provided. The method includes obtaining a depilatory wax additive, the depilatory wax additive having a molded hard wax composition and a scented component, and obtaining a depilatory wax composition having solid particles. The method further includes heating the depilatory wax composition to form a liquefied wax composition and mixing the depilatory wax additive with the liquefied wax composition to form a wax mixture. Finally, the method includes heating the wax mixture until the depilatory wax additive liquefies, such that the scented component is dispersed in the wax mixture to form a liquefied wax mixture having the scented component.

In some embodiments, the method includes applying the liquefied wax mixture to skin for hair removal. In some embodiments, the method includes removing the liquefied wax mixture from the skin to remove hair from the skin. In some embodiments, the weight ratio of the depilatory wax additive to the depilatory wax composition is 1:80 to 1:160.

In another embodiment, a depilatory wax additive is provided that includes a molded hard wax composition and a scented component. In some embodiments, the molded hard wax composition includes polycyclopentadiene, microcrystalline wax, an ethylene-vinyl acetate (VA) copolymer, paraffin, and calcium aluminum borosilicate.

In another embodiment, a method for using a depilatory wax composition is provided. The method includes obtaining a depilatory wax additive, the depilatory wax additive having a molded hard wax composition and a skin treatment, and obtaining a depilatory wax composition having solid particles. The method further includes heating the depilatory wax composition to form a liquefied wax composition and mixing the depilatory wax additive with the liquefied wax composition to form a wax mixture. Finally, the method includes heating the wax mixture until the depilatory wax additive liquefies, such that the skin treatment is dispersed in the wax mixture to form a liquefied wax mixture having the skin treatment.

In some embodiments, the method includes applying the liquefied wax mixture to skin for hair removal. In some embodiments, the method includes removing the liquefied wax mixture from the skin to remove hair from the skin. In some embodiments, the weight ratio of the depilatory wax additive to the depilatory wax composition is 1:80 to 1:160. In some embodiments, the skin treatment includes an anti-inflammatory or an exfoliant.

In another embodiment, a depilatory wax additive is provided that includes a molded hard wax composition and a skin treatment. In some embodiments, the molded hard wax composition includes polycyclopentadiene, microcrystalline wax, an ethylene-vinyl acetate (VA) copolymer, paraffin, and calcium aluminum borosilicate. In some embodiments, the skin treatment includes an anti-inflammatory or an exfoliant.

DETAILED DESCRIPTION

Figure 1:
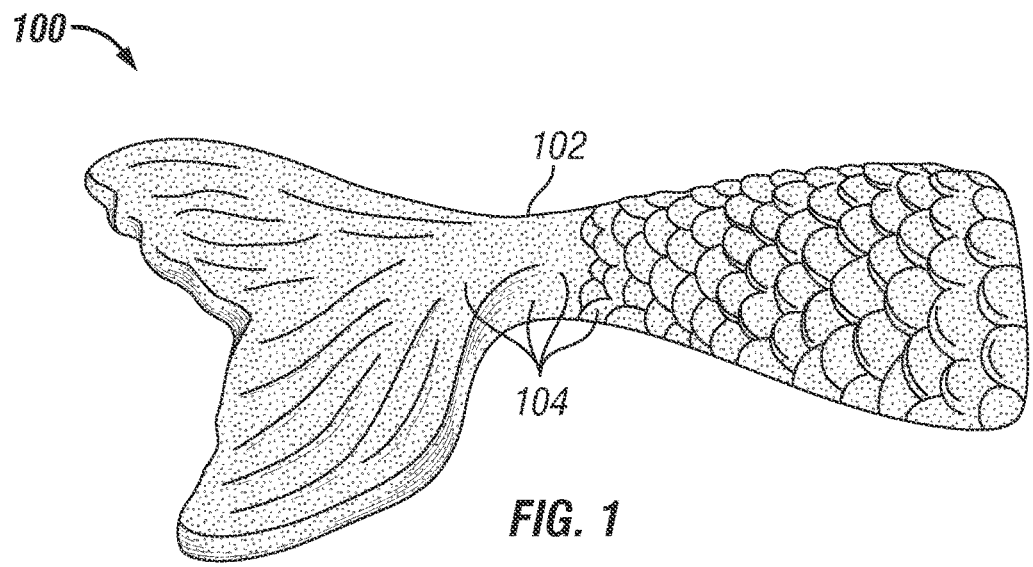
FIG. 1 is a drawing of a depilatory wax additive having a glitter component.

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

In some embodiments, a depilatory wax additive includes a molded hard wax composition having glitter, a color modifier, a scent modifier, a skin treatment, or any combination thereof. The depilatory wax additive may be added to a preexisting hard wax composition to add the glitter, a color modifier, a scent modifier, a skin treatment, or any combination thereof to the hard wax composition for use in the application of hair removal. In some embodiments, the molded hard wax composition of the depilatory wax additive may include polycyclopentadiene, microcrystalline wax (cera microcristallina), an ethylene-vinyl acetate (VA) copolymer, paraffin, and calcium aluminum borosilicate. In some embodiments, the molded hard wax composition of the depilatory wax additive may also include glyceryl rosinate, rosin (colophonium), beeswax (cera alba) and Mica.

In some embodiments, a depilatory wax additive includes a molded hard wax composition having glitter. The term "glitter" may refer to reflective particles. The glitter may be a different color or the same color as the molded hard wax composition of the depilatory wax additive, or a different color or the same color as the preexisting hard wax composition. The depilatory wax additive may be mixed with a preexisting hard wax composition to add glitter to the preexisting hard wax composition for use in hair removal. The molded hard wax composition may be molded into various shapes or sizes for ease of use and to provide for different concentrations of glitter. In some embodiments, the depilatory wax additive includes a wax to glitter ratio of about 3:1 to 5:1. In some embodiments, the weight ratio of depilatory wax additive to the preexisting hard wax composition may be at least 1 ounce to 5 pounds up to 2 ounces to 10 pounds. In some embodiments, the glitter may be formed a polymer (e.g., a plastic such as polyethylene terephthalate (PETE)) and a metal (e.g., aluminum). In some embodiments, the glitter may be formed from a biodegradable component (e.g., cellulose).

In some embodiments a process for using a depilatory wax additive that includes a molded hard wax composition having a concentration of glitter is provided. The process includes obtaining the molded hard wax composition having a concentration of glitter and obtaining a preexisting hard wax composition. The preexisting hard wax composition may be in the form of pellets, beads, or other solid particles. The preexisting hard wax composition may be heated until the hard wax composition forms a liquid. The depilatory wax additive may be added to the liquefied hard wax composition to form a wax mixture. The wax mixture may be stirred and heated (e.g., stirred and heated simultaneously) until the depilatory wax additive liquefies and the glitter is dispersed in the wax mixture. The wax mixture having the glitter may then be applied to the skin for hair removal, such that the glitter is visible in the applied wax mixture. After remaining on the skin for a time period, the hard wax mixture may be removed without a strip to remove hair.

In some embodiments, a depilatory wax additive includes a molded hard wax composition having a color modifier. The depilatory wax additive may be mixed with a hard wax to add color to a preexisting hard wax composition for use in hair removal. The molded hard wax composition may be molded into various shapes or sizes for ease of use and to provide for different concentrations of the color modifier. In some embodiments, the color modifier may be in an amount of 0.5 ounces to 2 ounces. In some embodiments, the preexisting hard wax composition may be a clear hard wax, such that the depilatory wax additive adds color to the clear hard wax composition. In other embodiments, the depilatory wax additive may be a first color, and the preexisting hard wax composition may be a second color, such that addition of the depilatory wax additive to the preexisting hard wax composition produces a different color than the first color and the second color. By way of example, adding a yellow depilatory wax additive to a red preexisting hard wax composition may produce an orange hard wax mixture. The color modifier may include a natural or synthetic dye, or other colored substance.

In some embodiments a process for using a depilatory wax additive that includes a molded hard wax composition having a color modifier is provided. The process includes obtaining the molded hard wax composition having a color modifier and obtaining a preexisting hard wax composition. The preexisting hard wax composition may be in the form of pellets, beads, or other solid particles. The preexisting hard wax composition may be heated until the hard wax composition forms a liquid. The depilatory wax additive may be added to the liquefied hard wax composition to form a wax mixture The wax mixture may be stirred and heated (e.g., stirred and heated simultaneously) until the depilatory wax additive liquefies and color is dispersed in the wax mixture, such that color of the preexisting hard wax composition is modified. The colored wax mixture may then be applied to the skin for hair removal. After remaining on the skin for a time period, the hard wax mixture may be removed without a strip to remove hair.

In some embodiments, a depilatory wax additive includes a molded hard wax composition having a scent modifier (e.g., a perfume, an oil, or other scented component). The depilatory wax additive may be mixed with a preexisting hard wax composition to modify the scent of a preexisting hard wax composition for use in hair removal or add a scent to a preexisting hard wax composition. The molded hard wax composition may be molded into various shapes or sizes for ease of use and to include different concentrations of the scent modifier. For example, in some embodiments, the preexisting hard wax composition may be an unscented hard wax composition. The depilatory wax additive having a scent modifier may be mixed with the unscented preexisting hard wax composition to produce a scented wax mixture.

In some embodiments a process for using a depilatory wax additive that includes a molded hard wax composition having a scent modifier is provided. The process includes obtaining the molded hard wax composition having a scent modifier and obtaining a preexisting hard wax composition. The preexisting hard wax composition may be in the form of pellets, beads, or other solid particles. The preexisting hard wax composition may be heated until the hard wax composition forms a liquid. The depilatory wax additive may be added to the liquefied hard wax composition to form a wax mixture. The wax mixture may be stirred and heated (e.g., stirred and heated simultaneously) until the depilatory wax additive liquefies and the scent modifier is dispersed in the wax mixture. The scented wax mixture may then be applied to the skin for hair removal. After remaining on the skin for a time period, the hard wax mixture may be removed without a strip to remove hair.

In some embodiments, a depilatory wax additive includes a molded hard wax composition having a skin treatment (e.g., moisturizer, an exfoliant, an anti-inflammatory, or other skin treatment, or combination thereof). The depilatory wax additive may be mixed with a preexisting hard wax composition to add the skin treatment to a preexisting hard wax composition for use in treatment during hair removal. The molded hard wax composition may be molded into various shapes or sizes for ease of use and to include different concentrations of the skin treatment. For example, in some embodiments the depilatory wax additive having a skin treatment modifier may be used to reduce or eliminate any irritation, inflammation, itchiness, or other discomfort caused by application of the preexisting hard wax composition when used without the depilatory wax additive.

In some embodiments a process for using a depilatory wax additive that includes a molded hard wax composition having a skin treatment is provided. The process includes obtaining the molded hard wax composition having a skin treatment and obtaining a preexisting hard wax composition. The preexisting hard wax composition may be in the form of pellets, beads, or other solid particles. The preexisting hard wax composition may be heated until the hard wax composition forms a liquid. The depilatory wax additive may be added to the liquefied hard wax composition to form a wax mixture. The wax mixture may be stirred and heated (e.g., stirred and heated simultaneously) until the depilatory wax additive liquefies and the skin treatment is dispersed in the wax mixture. The wax mixture having the skin treatment may then be applied to the skin for hair removal, such that the skin treatment is simultaneously applied to the skin with the wax mixture. After remaining on the skin for a time period, the hard wax mixture may be removed without a strip to remove hair. The skin treatment may reduce or eliminate any irritation, inflammation, itchiness, or other discomfort caused by the preexisting hard wax composition. In some embodiments, the skin treatment may provide improvements to the skin such as tightening, removal of discoloring, anti-aging, or rejuvenating.

In some embodiments, a depilatory wax additive may include a molded hard wax composition and any combination of glitter, color modifier, scent modifier, and skin treatment. For example, in some embodiments a depilatory wax additive may include a molded hard wax composition having glitter and a color modifier. In another embodiment, a molded hard wax composition may include a color modifier and a scent modifier.

FIG. 1 depicts a depilatory wax additive 100 that includes a molded hard wax composition 102 and glitter 104 in accordance with an embodiment of the disclosure. As shown in FIG. 1, the molded hard wax composition may be molded to a particular size and shape (e.g., a mermaid's tail) and may include glitter dispersed throughout the molded hard wax composition.

Figure 2:
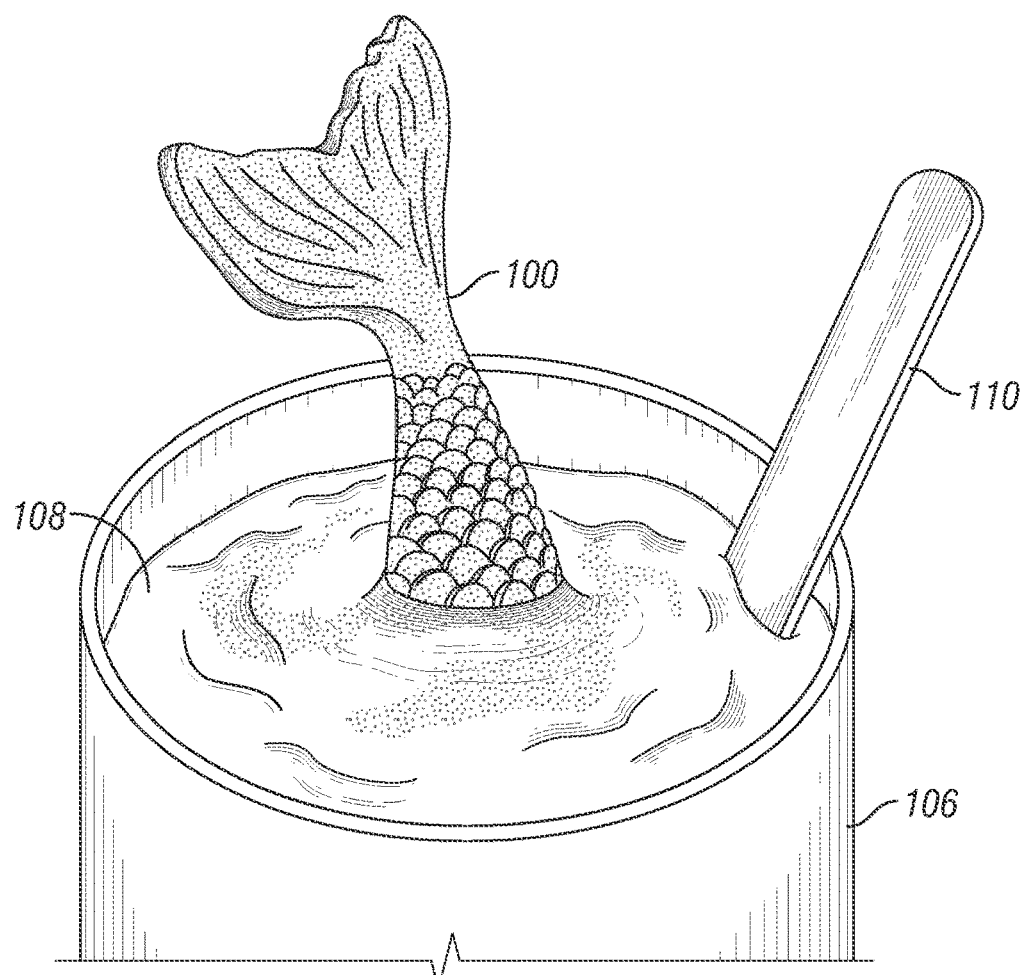
FIG. 2 is a drawing of a depilatory wax additive having a glitter component added to a liquefied hard wax composition.
Figure 3:
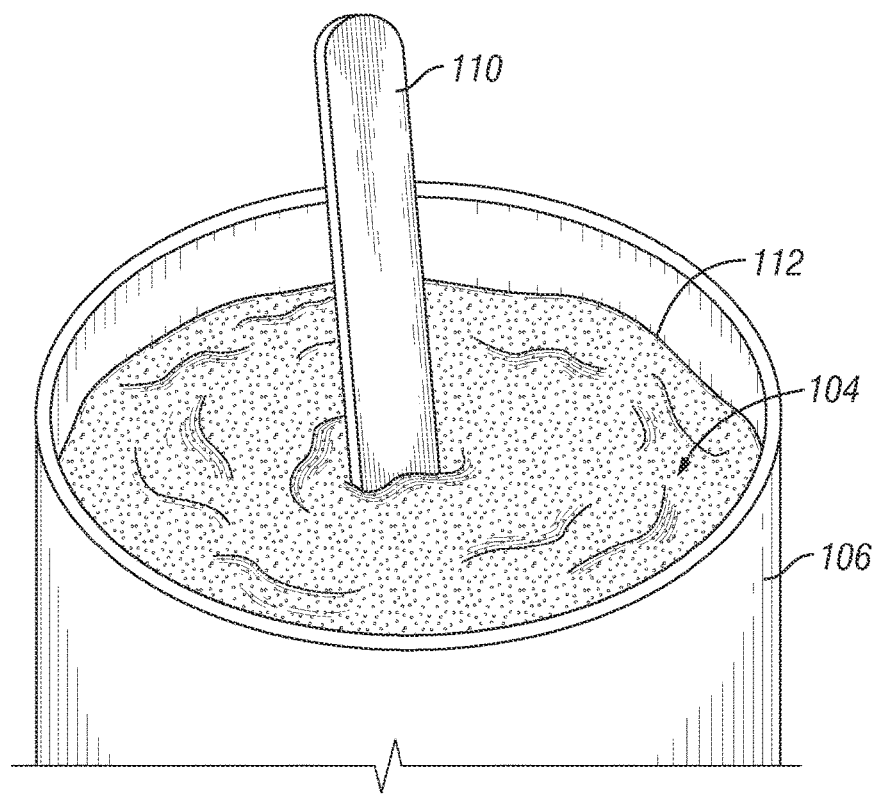
FIG. 3 is a drawing of a liquefied wax mixture formed from a hard wax composition and depilatory wax additive having a glitter component.

FIG. 2 depicts the mixing of the depilatory wax additive 100 in a container 106 of liquefied hard wax 108 without glitter in accordance with an embodiment of the disclosure. As discussed herein, the liquefied hard wax 108 may be formed from a preexisting hard wax composition of pellets, beads, or other solid particles by heating the hard wax composition (e.g., heating in a container) until it forms a liquid. The depilatory wax additive 100 may be added to liquefied hard wax 108 and heated and stirred (e.g., via paddle 110) until the depilatory wax additive 100 liquefies and mixes with the liquefied hard wax 108 to form a wax mixture FIG. 3 depicts a wax mixture 112 in the container 102 formed the mixing shown in FIG. 2 in accordance with an embodiment of the disclosure. As shown in FIG. 3, the glitter 102 from the depilatory wax additive 100 is dispersed relatively uniformly in the wax mixture 112.

Figure 4:
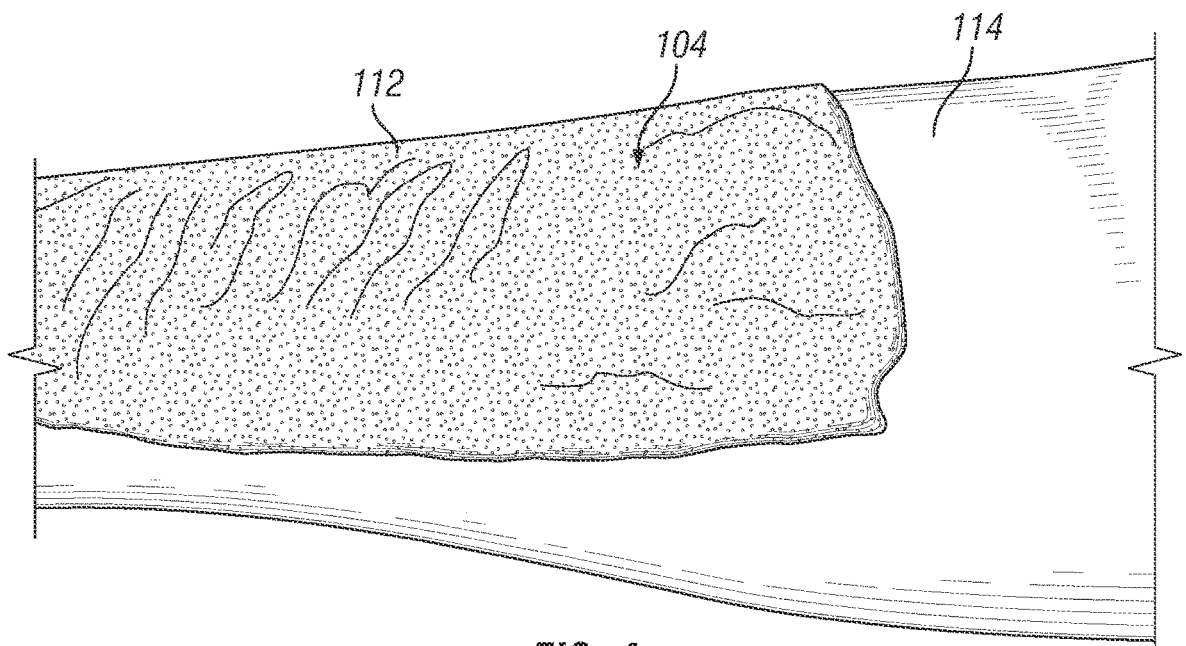
FIG. 4 is a drawing of a liquefied wax mixture formed from a hard wax composition and depilatory wax additive having a glitter component as applied to skin for hair removal.

FIG. 4 depicts the application of the wax mixture 112 having glitter 102 to skin 114 in accordance with an embodiment of the disclosure. The application of the wax mixture 112 maintains the relatively uniform dispersal of the glitter 102 such that the glitter is visible in the applied wax mixture. After remaining on the skin for a suitable time period, the wax mixture 112 may be removed without a strip to remove hair.

Figure 5:
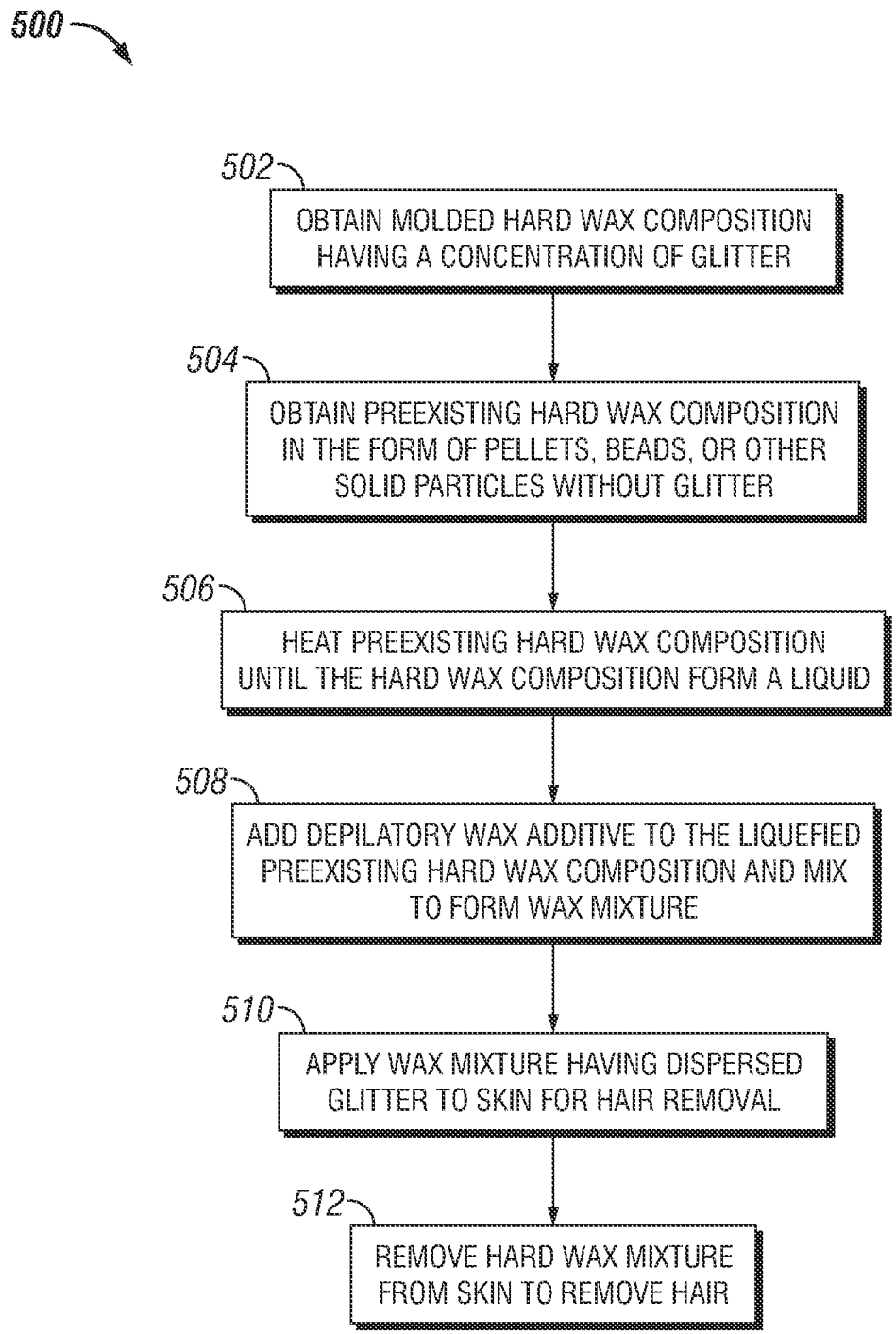
FIG. 5 is a flowchart of a process for using a depilatory wax additive that includes a molded hard wax composition and glitter in accordance with an embodiment of the disclosure.

FIG. 5 depicts a process 500 for using a depilatory wax additive that includes a molded hard wax composition and glitter in accordance with an embodiment of the disclosure. It should be appreciated that the process 500 described in FIG. 5 may also be applicable to a color modifier, a scent modifier, a skin treatment instead of or in combination with the glitter or each other. As shown in FIG. 5, a molded hard wax composition having a concentration of glitter may be obtained (block 502). A preexisting hard wax composition (e.g., an "off-the-shelf" product) in the form of pellets, beads, or other solid particles without glitter may also be obtained (block 504). The preexisting hard wax composition may be heated until the hard wax composition forms a liquid (block 506). In some embodiments, the preexisting hard wax composition may be heated to a temperature of about 130° F. (54.4° C.).

The depilatory wax additive may be added to the liquefied preexisting hard wax composition, mixed via stirring (e.g., manual stirring with a paddle, spoon, or other device), and heated until the depilatory wax additive liquefies and mixes with the liquefied preexisting hard wax composition to form a wax mixture such that the glitter is dispersed in the wax mixture (block 508). In some embodiments, the wax mixture such may be heated to a temperature of about 130° F. (54.4° C.). The wax mixture having the dispersed glitter may then be applied to the skin for hair removal via an applicator (block 510), such that the glitter is visible in the applied wax mixture. After remaining on the skin for a suitable time period (e.g., until the hard wax mixture cools and becomes soft and pliable), the hard wax mixture may be removed without a strip to remove hair (block 512).

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method for using a depilatory wax composition, comprising:
    obtaining a depilatory wax additive, the depilatory wax additive comprising a molded hard wax composition and glitter;
    obtaining a depilatory wax composition, the depilatory wax composition comprising solid particles;
    heating the depilatory wax composition to form a liquefied wax composition;
    simultaneously mixing and heating the depilatory wax additive with the liquefied wax composition until the depilatory wax additive liquefies, such that the glitter is dispersed in the resultant liquefied wax mixture; and
    applying the liquified wax mixture to skin for hair removal.

2. The method of claim 1, comprising removing the liquefied wax mixture from the skin to remove hair from the skin.

3. The method of claim 1, wherein the depilatory wax additive has a hard wax to glitter volumetric ratio of 3:1 to 5:1.

4. The method of claim 1, wherein the weight ratio of the depilatory wax additive to the depilatory wax composition is 1:80 to 1:160.

5. A method for using a depilatory wax composition, comprising:
    obtaining a depilatory wax additive, the depilatory wax additive comprising a molded hard wax composition and a component selected from the group consisting of a color component or a scented component;
    obtaining a depilatory wax composition, the depilatory wax composition comprising solid particles;
    heating the depilatory wax composition to form a liquefied wax composition;
    simultaneously mixing and heating the depilatory wax additive with the liquefied wax composition until the depilatory wax additive liquefies so to form a liquefied wax mixture; and
    applying the liquified wax mixture to skin for hair removal.

6. The method of claim 5, wherein the weight ratio of the depilatory wax additive to the depilatory wax composition is 1:80 to 1:160.

7. A method for using a depilatory wax composition, comprising:

obtaining a depilatory wax additive, the depilatory wax additive comprising a molded hard wax composition and a skin treatment;

obtaining a depilatory wax composition, the depilatory wax composition comprising solid particles;

heating the depilatory wax composition to form a liquefied wax composition;

simultaneously mixing and heating the depilatory wax additive with the liquefied wax composition until the depilatory wax additive liquefies such that the skin treatment is dispersed in the resultant liquefied wax mixture; and and applying the liquified wax mixture to skin for hair removal.

8. The method of claim 7, wherein the skin treatment comprises an anti-inflammatory or an exfoliant.

* * * * *